United States Patent [19]

Obayashi et al.

[11] Patent Number: 5,843,755
[45] Date of Patent: Dec. 1, 1998

[54] GROUP OF ANTITUMOR COMPOUNDS AND METHOD FOR PRODUCING THE SAME

[75] Inventors: Yoko Obayashi; Toshihiko Yoshimura; Yuka Ikenoue; Ryosuke Fudo; Masahiro Murata; Toshihiko Ando, all of Kawasaki, Japan

[73] Assignee: Ajinomoto Co., Inc., Tokyo, Japan

[21] Appl. No.: 849,220

[22] PCT Filed: Mar. 14, 1997

[86] PCT No.: PCT/JP97/00827

§ 371 Date: Jun. 10, 1997

§ 102(e) Date: Jun. 10, 1997

[87] PCT Pub. No.: WO97/44479

PCT Pub. Date: Nov. 27, 1997

[30] Foreign Application Priority Data

May 20, 1996 [JP] Japan .................................. 8-124530

[51] Int. Cl.$^6$ .............................. C12N 1/14; C12N 1/15; A61K 31/095; A61K 31/12
[52] U.S. Cl. ................. 435/243; 435/254.1; 435/254.11; 514/550; 514/675; 514/706; 514/740
[58] Field of Search .................................. 435/243, 254.1, 435/254.11; 514/740, 706, 675, 550

[56] References Cited

FOREIGN PATENT DOCUMENTS 45-9832  4/1970  Japan .

OTHER PUBLICATIONS

Junji Magae et al. Antitumor and Antimetastatic Activity of an Antibiotic, Ascofuranone, and Activation Phagocytes the Journal of Antibiotics (1988), vol. 41, No. 7, pp. 959–965.

Junji Magae et al. Differentiation of Mouse and Human Myeloid Leukemia Cells Induced by Antitumor Antibiotic, Ascofuranone Agric. Biol. Chem. (1988), vol. 52, No. 12, pp. 3143–4147.

*Primary Examiner*—Nancy Degen
*Attorney, Agent, or Firm*—Oblon, Spivak, McClelland, Maier & Neustadt, P.C.

[57] ABSTRACT

A mold belonging to the genus Ascochyta is cultivated with a medium to obtain a culture. A compound having a structure represented by the following formula and having an antitumor activity, which is capable of forming a tautomeric equilibrium mixture composed of tautomers, is collected from the culture, or a mixture of the tautomers is collected from the culture.

10 Claims, 5 Drawing Sheets

GROUP OF ANTITUMOR COMPOUNDS AND METHOD FOR PRODUCING THE SAME

TECHNICAL FIELD

The present invention relates to a novel compound and a method for producing the compound. In particular, the present invention relates to a compound having an antitumor activity and produced by a mold belonging to the genus Ascochyta.

BACKGROUND ART

Many compounds have been hitherto reported as antitumor antibiotics, such as anthracyclines and mitomycins.

DISCLOSURE OF THE INVENTION

An object of the present invention is to provide a novel antitumor substance and a method for producing the substance.

The present inventors have found out a group of novel compounds produced by a mold belonging to the genus Ascochyta, and found out that the group of compounds have an antitumor activity. Thus the present invention has been completed.

The compound provided by the present invention is represented by the following structural formula:

The compound represented by the foregoing structural formula involves a plurality of tautomers. Of the tautomers, a first compound is designated as FE399-P1, which is capable of forming a major component of a tautomeric equilibrium mixture having the following physicochemical properties.

(1) Appearance of dry preparation: white powder.

(2) Melting point: 260° to 265° C. (decomposition).

(3) Solubility: readily soluble in pyridine and acetic acid, soluble in dimethyl sulfoxide, chloroform, ethyl acetate, methanol, and acetonitrile, and scarcely soluble in water.

(4) Ultraviolet absorption spectrum: end absorption appears in the vicinity of 200 nm in an acetonitrile solution.

(5) Chemical shift values ($\delta$, unit: ppm) obtained by $^1$H nuclear magnetic resonance spectrum (600 MHz, pyridine-$d_5$):

9.55 (1H, s), 7.97 (1H, d), 5.84 (1H, t), 5.19 (1H, brs), 4.88 (1H, s), 4.04 (2H, m), 3.65 (1H, d), 3.47 (1H, d), 2.56 (1H, t), 2.37 (1H, t), 2.12 (1H, m), 1.11–1.51, 0.83 (1H, t).

(6) Chemical shift values ($\delta$, unit: ppm) obtained by $^{13}$C nuclear magnetic resonance spectrum (150 MHz, solvent: pyridine-$d_5$):

176.001, 174.731, 171.733, 75.383, 55.235, 55.114, 47.820, 45.354, 36.572, 35.866, 32.780, 26.992, 26.932, 25.349, 22.492, 19.208, 14.109.

(7) Chemical shift values ($\delta$, unit: ppm) obtained by $^{13}$C nuclear magnetic resonance spectrum (100 MHz, solvent: DMSO-$d_6$):

174.8, 173.1, 170.3, 74.2, 53.5, 52.6, 47.4, 44.1, 36.0, 34.9, 32.3, 26.9, 26.6, 26.6, 24.8, 21.6, 18.3, 13.7.

(8) Color reaction color development with phosphomolybdic acid: positive; color development with anisaldehyde: positive.

(9) The first compound is separated on thin layer chromatography under the following development condition:

adsorbent: Kieselgel 60 F254, thickness: 0.25 mm;
solvent for development: chloroform:methanol=93:7;
Rf value: about 0.32.

A second compound provided by the present invention is designated as FE399-P2. The compound is capable of forming a tautomeric equilibrium mixture together with FE399-P1. The second compound is separated on thin layer chromatography under the following development condition:

adsorbent: Kieselgel 60 F254, thickness: 0.25 mm;
solvent for development: chloroform:methanol=93:7;
Rf value: about 0.42.

A third compound provided by the present invention is designated as FE399-P3. There is high possibility that FE399-P3 is capable of forming a tautomeric equilibrium mixture together with FE399-P1 and/or FE399-P2 described above. However, there remains possibility that FE399-P3 might be a partially decomposed product of FE399-P1 or FE399-P2. The third compound is separated on thin layer chromatography under the following development condition:

adsorbent: Kieselgel 60 F254, thickness: 0.25 mm;
solvent for development: chloroform:methanol=93:7;
Rf value: about 0.54.

In another aspect of the present invention, there is provided a tautomeric equilibrium mixture comprising two or three species selected from FE399-P1, FE399-P2, and FE399-P3 described above.

In still another aspect of the present invention, there is provided a method for producing the compound or the mixture described above, comprising the steps of cultivating a mold belonging to the genus Ascochyta with a medium, and collecting, from an obtained culture, a tautomeric equilibrium mixture comprising FE399-P1, FE399-P2, or FE399-P3, or two or three species of them.

In still another aspect of the present invention, there is provided a pharmaceutical composition containing an effective component of one species selected from FE399-P1, FE399-P2, and FE399-P3 described above, or a mixture of effective components of two or more species selected from FE399-P1, FE399-P2, and FE399-P3 described above.

In the following description, FE399-P1, FE399-P2, or FE399-P3 is referred to as "FE399 compound", and the tautomeric equilibrium mixture containing two or three species of them is referred to as "group of FE399 compounds" or "FE399 compound group", if necessary.

The present invention will be explained in detail below.

The group of FE399 compounds of the present invention are obtained by collecting the compounds from a culture of the mold belonging to the genus Ascochyta. The mold belonging to the genus Ascochyta includes, for example, Ascochyta sp. AJ 117309 strain (FERM BP-5517) separated by the present inventors. AJ 117309 strain was separated from a raw leaf of *Taxus cuspidata* var. nana Rehd. (plant belonging to Taxaceae) as follows.

A healthy leaf of *Taxus cuspidata* var. nana Rehd. collected in Kawasaki-shi, Kanagawa-ken, Japan was used as a sample. Dust and dirt on the surface of the leaf were removed with flowing water, and then the surface was sterilized with 60% ethanol for 1 minute. The leaf was immediately washed with sterilized water, and then it was cut with a sterilized knife into small sections of 1 cm square. Two of the sections were placed on an LCA medium (glucose 1 g/L, $KH_2PO_4$ 1 g/L, $MgSO_4.7H_2O$ 0.2 g/L, KCl 0.2 g/L, $NaNO_3$ 2 g/L, yeast extract 0.2 g/L, agar 15 g/L, pH 6.5) so that they were separated from each other by 3 to 4 cm, followed by cultivation at room temperature. On fourth or fifth day, an elongating hypha over the medium was picked up at its tip with a thin needle, and it was transferred onto a new medium to perform purification. Microbiological properties of AJ 117309 strain thus separated are described below.

(a) Growth Situation on Various Media

Growth on a malt extract agar medium is vigorous and rapid, providing a colony diameter of 45 mm at 25° C. for 5 days. The front surface of a colony is white and cottony. The back surface is initially white, and then a part of it becomes dark green. Neither pigment exudation into the medium nor droplet formation is observed.

Growth on a potato glucose agar medium is vigorous and rapid, providing a colony diameter of 42 mm at 25° C. for 5 days. The front surface of a colony is white and cottony. The back surface is initially white, and then a part of it becomes dark green. Formation of neither pigment nor droplet is observed.

Growth on a cornmeal agar medium is good, providing a colony diameter of 43 mm at 25° C. for 5 days. The surface of a colony is white and cottony, having a relatively thin substrate mycelium layer. Neither pigment exudation into the medium nor droplet formation is observed.

Formation of conidiomata is not observed on the media described above (however, the fungus rarely produces pycnidioid conidiomata in the agar). However, when the mold is cultivated with a natural substrate (such as sterilized plant leaves) placed on the medium, formation of pycnidia is distinctly observed on the leaf piece. No perfect stage has been observed under any of the conditions described above.

(b) Morphological Nature

Pycnidia formed on a leaf piece placed on a malt extract agar medium are dark green, and spherical or subspherical, with a diameter of 0.3 to 0.5 mm, having ostioles at the center. Upon maturation, a mass of white and creamy spores are discharged from the ostioles. Conidia are colorless, elliptic or oval, and bicellular (with a central septum), having a size of (6.0 to 10.0)×(2.0 to 2.5) $\mu$m.

The growable temperature is 10° to 35° C., and the optimum growable temperature is 22° to 27° C. The growable pH is 3 to 10.

Judging from the microbiological properties described above, the present strain has been clarified to belong to Deuteromycotina, Coelomycetes, Ascochyta in accordance with "The Coelomycetes" (1980, Commonwealth Mycological Institute (England), written by B. C. Sutton). The present strain has been designated as Ascochyta sp. AJ 117309 strain. The present strain has been internationally deposited on the basis of the Budapest Treaty since Apr. 23, 1996 in National Institute of Bioscience and Human Technology of Agency of Industrial Science and Technology (postal code: 305, 1-3 Higashi-Icchome, Tsukuba-shi, Ibaraki-ken, Japan), and awarded a deposition number of FERM BP-5517.

The group of FE399 compounds are obtained by cultivating, with a medium, the mold belonging to the genus Ascochyta such as AJ 117309 described above, and collecting the compounds from an obtained culture.

The mold belonging to the genus Ascochyta is cultivated, for example, as follows. A malt extract agar medium is inoculated with the mold belonging to the genus Ascochyta to perform cultivation at 25° C. for 7 days. Agar pieces are excised from the malt extract agar medium, and a Roux flask containing a production medium having the following composition is inoculated therewith to perform cultivation stationarily at 25° C. for about 3 weeks.

TABLE 1

| (Composition of production medium / Roux flask) | |
|---|---|
| Oatmeal | 20 g |
| Liquid medium* | 28 ml |

*:Composition of liquid medium
Glucose 2 g/L
Fructose 5
Sucrose 8
NZ amine 2
$MgSO_4.7H_2O$ 0.5
KCl 0.5
$ZnSO_4.7H_2O$ 0.5
$KH_2PO_4$ 1
(pH 6.0)

The mold belonging to the genus Ascochyta is cultivated as described above, and then acetone is added in an amount of 100 ml per one Roux flask to perform extraction at room temperature for 30 minutes. An acetone layer is recovered, and then acetone is distilled off by concentrating the recovered solution under a reduced pressure. Water is added to an obtained residue to give an aqueous solution. The aqueous solution is extracted with an equal volume of ethyl acetate three times. An obtained ethyl acetate-extracted solution is washed with a saturated sodium chloride aqueous solution, followed by dehydration with anhydrous sodium sulfate. The resulting solution is concentrated under a reduced pressure. An obtained residue is dissolved in methanol, followed by addition of a 1.2 volume of hexane to perform an extracting operation. After a hexane layer is removed, a methanol layer is concentrated and dried up. An obtained residue is dissolved in ethyl acetate, followed by being stationarily left to stand at 4° C. for several days to deposit crystals. After that, matters dissolved in ethyl acetate are removed by means of a centrifugation operation. A residue thus obtained is washed with a small amount of methanol. As a result, a crude purified preparation is obtained, which contains a major component of FE399-P2, and contains small amounts of FE399-P1 and FE399-P3.

Next, the crude purified preparation obtained as described above is suspended in acetonitrile, followed by being left to stand at room temperature for about 1 day. As a result, a preparation is obtained, which contains a major component of FE399-P1, and contains small amounts of FE399-P2 and FE399-P3.

The FE399 compounds contained in the crude purified preparation can be confirmed, for example, by means of thin layer chromatography. Kieselgel 60 F254 (thickness: 0.25 mm, produced by Merk) may be used as an adsorbent, and chloroform:methanol=93:7 may be used as a solvent for development. Under this condition, Rf values of FE399-P1, FE399-P2, and FE399-P3 are about 0.32, 0.42, and 0.54 respectively in this order.

Figure 1:
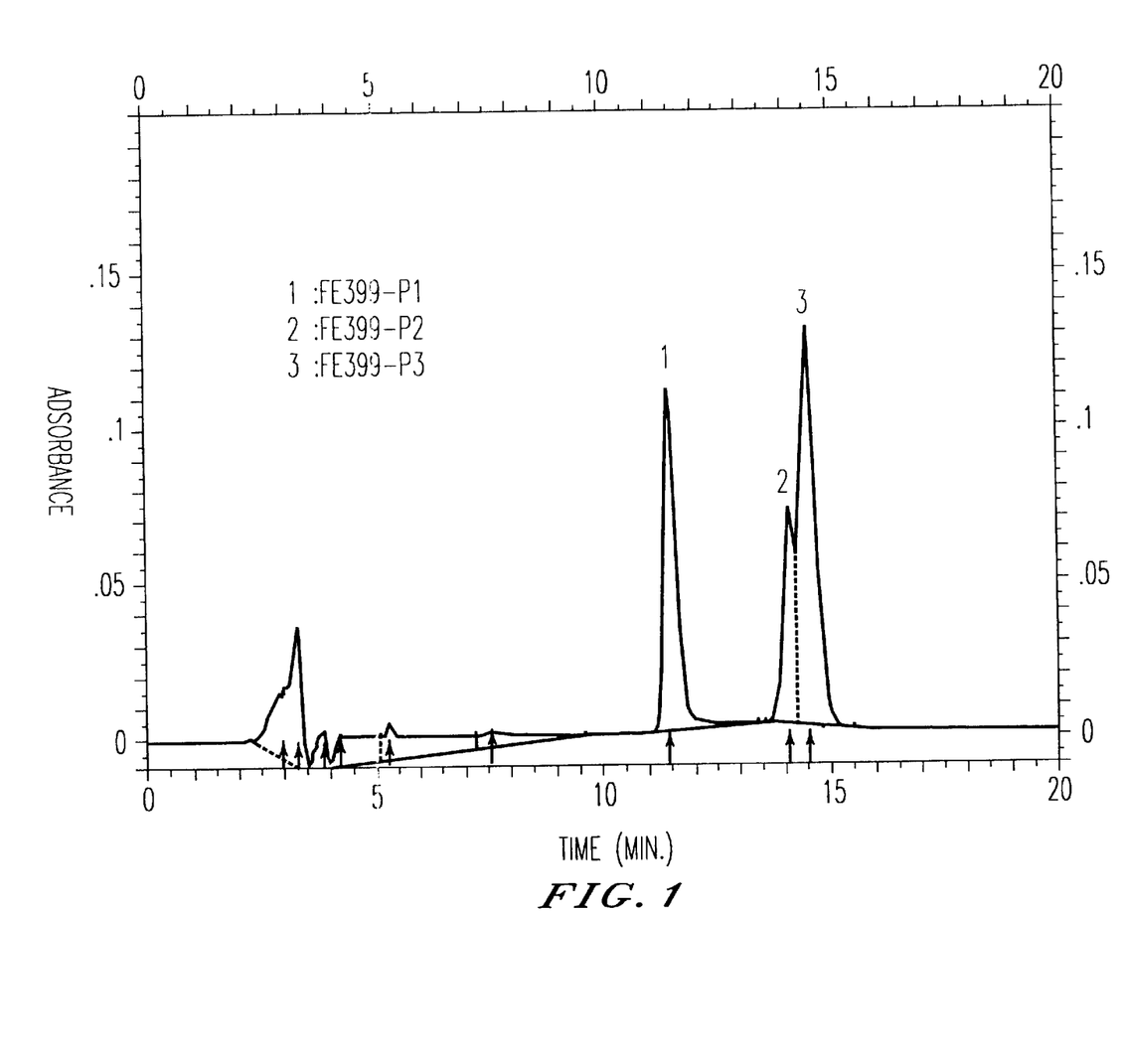
FIG. 1 shows a chromatogram of reversed phase high performance liquid chromatography for a group of FE399 compounds.

The group of FE399 compounds can be separated, for example, by using reversed phase high performance liquid chromatography. When reversed phase high performance liquid chromatography is performed under a condition shown in Table 2, the respective FE399 compounds have retention times as shown below. A chromatogram obtained under this condition is shown in FIG. 1. In FIG. 1, peaks 1, 2, and 3 correspond to FE399-P1, FE399-P2, and FE399-P3 respectively.

TABLE 2

| Instruments used: | |
| --- | --- |
| UV detector: | Waters 991 (produced by Waters) |
| Pump: | HITACHI L-6200 (produced by Hitachi) |
| Column: | |
| Analyzing reversed phase high performance liquid chromatography column (CAPCELL PAK C18 UG120 5 μm, 4.6 mmφ × 250 mm (produced by Shiseido) | |
| Solvent for elution: | 50% acetonitrile |
| Flow rate: | 0.8 ml/minute |
| Retention time (unit: minute): | |
| FE399-P1: | about 9.1 |
| FE399-P2: | about 11.7 |
| FE399-P3: | about 12.1 |

The FE399 compounds form a tautomeric equilibrium mixture comprising at least two or three species in an organic solvent such as acetonitrile, chloroform, and acetic acid. The major component of the tautomeric equilibrium mixture changes depending on conditions such as the solvent and the temperature. Among the group of the compounds, FE399-P1 is relatively stable. The physicochemical properties of the FE399 compound described above (except for the Rf values obtained in the thin layer chromatography) are those relevant to FE399-P1 separated by high performance liquid chromatography. However, there is some possibility that small amounts of FE399-P2 and FE399-P3 are contained in the sample used.

Of the FE399 compounds, at least FE399-P1 and FE399-P2 are tautomers represented by the same planar structural formula (the chemical formula described above). There is every possibility that FE399-P3 is also a tautomer, however, it is impossible to deny the possibility that FE399-P3 is a partially decomposed product of FE399-P1 or FE399-P2.

The group of FE399 compounds and the purified FE399 compounds may be stored under a condition including, for example, a condition for storage in a dry state at −20° C.

The FE399 compounds of the present invention have an antitumor activity. Accordingly, the compounds are expected to be used as an effective component of pharmaceutical compositions for treating solid cancers and leukemia.

BEST MODE FOR CARRYING OUT THE INVENTION

The present invention will be more specifically explained below with reference to Examples.

EXAMPLE 1

Production of FE399 Compounds

Ascochyta sp. AJ 117309 strain was inoculated to a malt extract agar medium to perform cultivation at 25° C. for 7 days. In the meantime, the production medium having the composition shown in Table 1 described above was prepared. The prepared medium was dispensed into 133 Roux flasks each having a volume of 500 mL, followed by being heated and sterilized at 120° C. for 20 minutes. Now agar pieces (diameter: 8 mm) were excised from the malt extract agar medium having been subjected to cultivation as described above. The production medium was inoculated with the agar pieces to perform cultivation stationarily at 25° C. for 21 days.

AJ 117309 strain was cultivated in accordance with the procedure described above, and then acetone was added to the Roux flasks in an amount of 100 ml per one flask. Extraction was performed at room temperature for 30 minutes, and an acetone layer was recovered. After that, acetone was distilled off by means of concentration under a reduced pressure. Water was added to an obtained residue to give an aqueous solution of 2 L. The aqueous solution was extracted with 2 L of ethyl acetate three times. An obtained ethyl acetate-extracted solution was washed with an aqueous solution of saturated sodium chloride, and then it was dehydrated with anhydrous sodium sulfate, followed by concentration under a reduced pressure.

After an obtained residue was dissolved in 500 ml of methanol, 600 ml of hexane was added thereto, to perform an extracting operation. A hexane layer was removed, and then a methanol layer was concentrated and dried up. An obtained residue was dissolved in 100 ml of ethyl acetate, followed by being left to stand stationarily at 4° C. for 2 days to deposit crystals. After that, matters dissolved in ethyl acetate were removed by means of a centrifugation operation. A residue thus obtained was washed with a small amount of methanol to obtain a crude purified preparation (190 mg). The crude purified preparation thus obtained was separated by means of thin layer chromatography (solvent for development: chloroform:methanol=93:7) by using Kieselgel 60 F254 (thickness: 25 mm, produced by Merk) as an adsorbent. The plate was stained with 5% phosphomolybdic acid ethanol solution. As a result, spots of three components were detected at Rf values of 0.32, 0.42, and 0.54. The components were designated as FE399-P1, FE399-P2, and FE399-P3 respectively in this order. FE399-P2 was a major component in the crude purified preparation. When the crude purified preparation was suspended in acetonitrile, and left to stand at room temperature for 20 hours, the major component was changed to FE399-P1.

The mixture containing the major component of FE399-P1 obtained as described above was concentrated under a reduced pressure. After that, a concentrated solution was subjected to separation by using preparative reversed phase high performance liquid chromatography (column: Capcell pak C18 SG120 Å, 10 mmφ×250 mm, produced by Shiseido; solvent for elution: 53% acetonitrile solution (flow rate: 3.5 ml/minute); UV detector: Waters 991 (produced by Waters); pump: HITACHI L-6200 (produced by Hitachi)) to fractionate and collect FE399-P1 and FE399-P2. FE399-P1 had a retention time of 7.5 minutes, and FE399-P2 had a retention time of 9.7 minutes.

EXAMPLE 2

Structural Analysis for FE399 Compounds

FE399-P1 isolated in accordance with the method described in Example 1 was dissolved in chloroform, and left to stand at room temperature for several hours. After that, an obtained sample was developed on thin layer chromatography under the same condition as that described above. As a result, the sample was separated into the spots of FE399-P1, FE399-P2, and FE399-P3. The respective spots were scraped off from the thin layer plate, and subjected to extraction with a solvent (chloroform:methanol= 50:50) to obtain the FE399 compounds which were independently separated again by means of thin layer chromatography under the same condition respectively. As a result, the three spots of FE399-P1, FE399-P2, and FE399-P3 were obtained. Further, FE399-P1 was dissolved in chloroform and left to stand at room temperature for several hours in the same manner as described above, and an obtained sample was subjected to analyzing reversed phase high performance liquid chromatography under the condition shown in Table 2 described above. As a result, the peaks corresponding to the respective FE399 compounds were observed. In this experiment, the respective FE399 compounds had the retention times exactly as shown in Table 2.

According to the results obtained in Example 2 in view of the results obtained in Example 1, it was judged that FE399-P1, FE399-P2, and FE399-P3 formed the tautomeric equilibrium mixture. However, it is impossible to deny the possibility that FE399-P3 was a partially decomposed product of FE399-P1 or FE399-P2.

Figure 2:
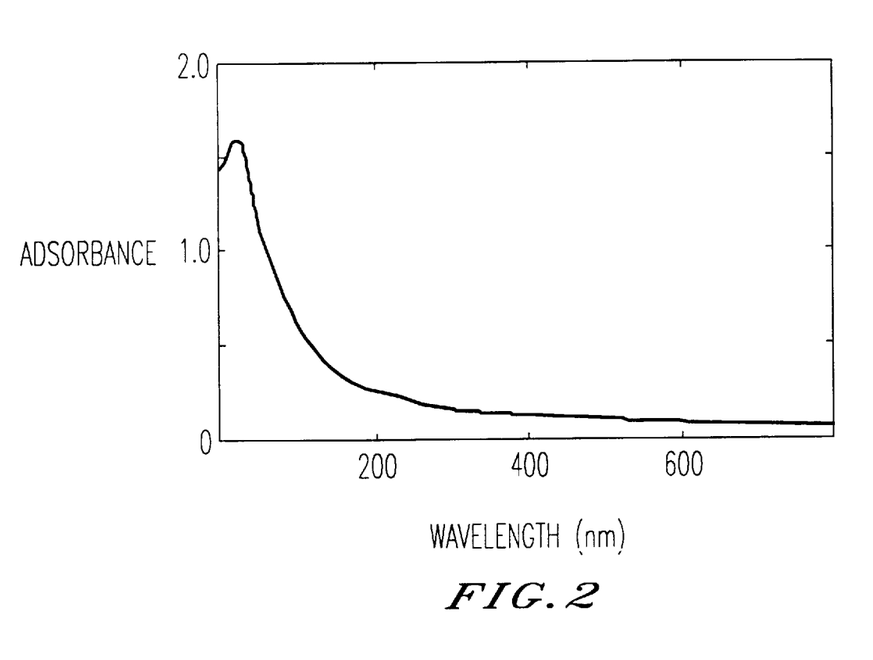
FIG. 2 shows an ultraviolet absorption spectrum of a tautomeric equilibrium mixture containing a major component of FE399-P1.
Figure 3:
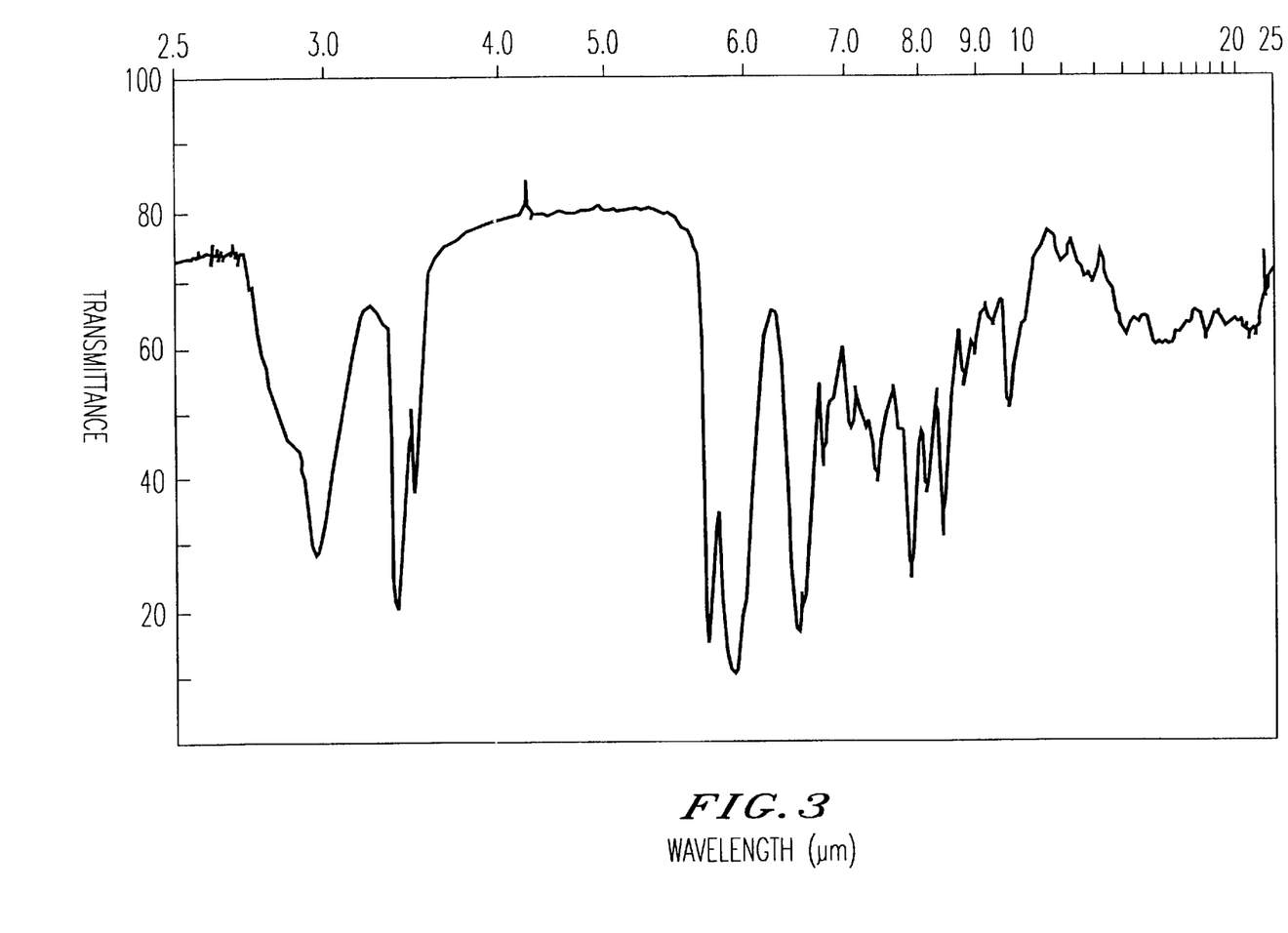
FIG. 3 shows an infrared absorption spectrum of the tautomeric equilibrium mixture containing the major component of FE399-P1.
Figure 4:
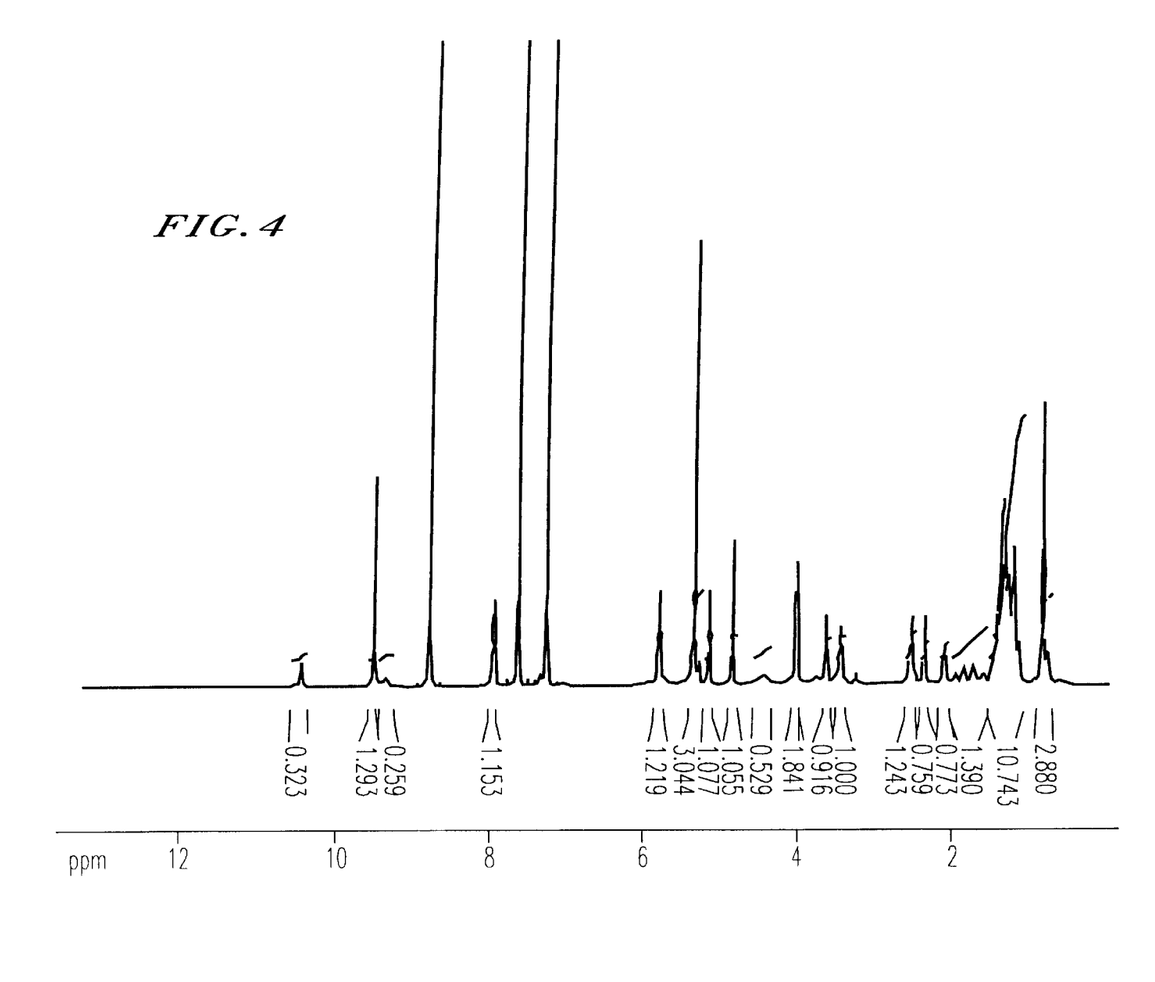
FIG. 4 shows a $^1$H nuclear magnetic resonance spectrum of the tautomeric equilibrium mixture containing the major component of FE399-P1.
Figure 5:
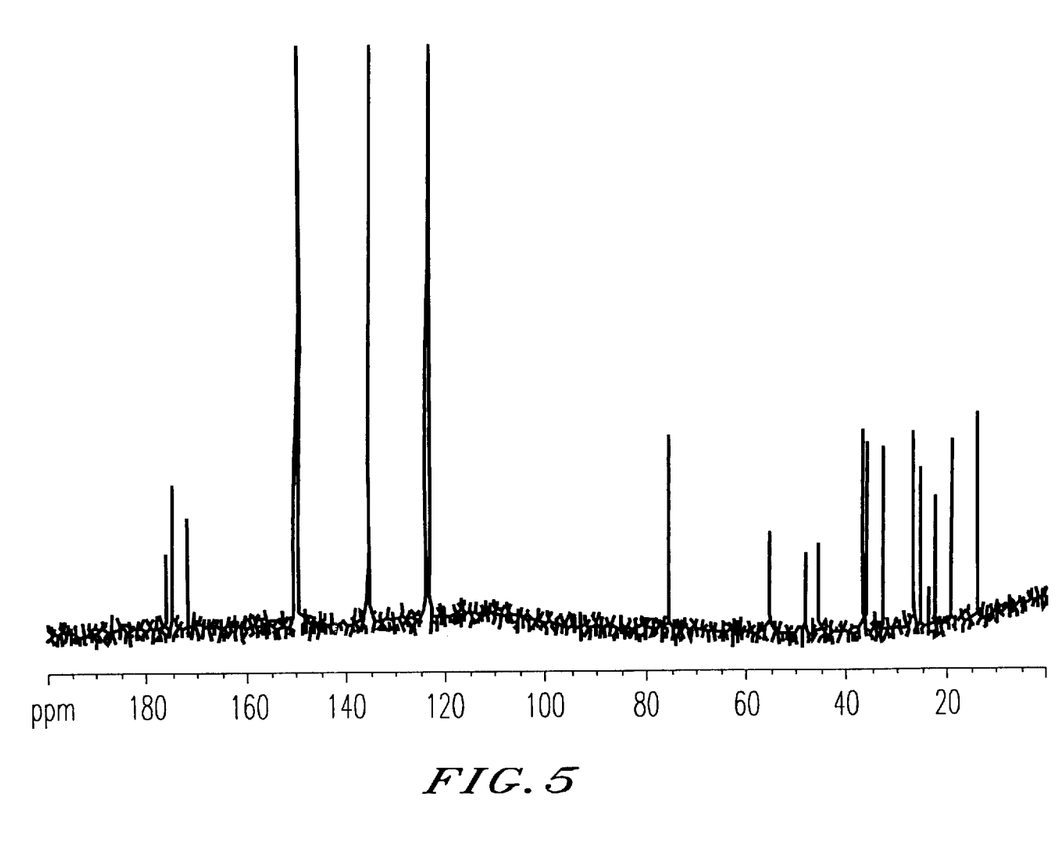
FIG. 5 shows a $^{13}$C nuclear magnetic resonance spectrum of the tautomeric equilibrium mixture containing the major component of FE399-P1.

Values of physicochemical properties of FE399-P1 (or the tautomeric equilibrium mixture containing FE399-P1 as the major component) obtained in Example 1 are exactly those described above. An ultraviolet absorption spectrum (measured by using UV-160 produced by Shimadzu) is shown in FIG. 2, and an infrared absorption spectrum obtained by using potassium bromide (measured by using IR-810 produced by JASCO) is shown in FIG. 3. A $^1$H nuclear magnetic resonance (NMR) spectrum and a $^{13}$C nuclear magnetic resonance spectrum (any of them was measured by using pyridine-$d_5$ as a solvent and using DMX 600 produced by Brucker) are shown in FIGS. 4 and 5 respectively.

According to the respective analytical values obtained in the foregoing analysis and a $^{13}$C nuclear magnetic resonance spectrum (100 MHz, solvent: DMSO-$d_6$), the structure of FE399-P1 was determined as represented by the following structural formula. The corresponding relationship between carbons and signals obtained in the $^{13}$C nuclear magnetic resonance spectrum (100 MHz, solvent: DMSO-$d_6$) is shown in Table 3.

TABLE 3

| Carbon | $^{13}$C-NMR (δ/ppm) |
|---|---|
| 1 | 173.1 C=O |
| 2 | 34.9 CH$_2$ |

TABLE 3-continued

| Carbon | $^{13}$C-NMR (δ/ppm) |
|---|---|
| 3 | 24.8 CH$_2$ |
| 4 | 26.6 CH$_2$ |
| 5 | 26.6 CH$_2$ |
| 6 | 26.9 CH$_2$ |
| 7 | 21.6 CH$_2$ |
| 8 | 32.3 CH$_2$ |
| 9 | 74.2 CH |
| 10 | 36.0 CH$_2$ |
| 11 | 18.3 CH$_2$ |
| 12 | 13.7 CH$_3$ |
| 13 | 170.3 C=O |
| 14 | 53.5 CH |
| 15 | 44.1 CH$_2$ |
| 16 | 174.8 C=O |
| 17 | 52.6 CH |
| 18 | 47.4 CH$_2$ |

EXAMPLE 3

Growth-Inhibiting Action of FE399 Compounds on Various Cells

The proliferation-inhibiting action of FE399 compounds obtained by purification, on various cells was measured under a condition shown below.

Various cells at concentrations shown in Table 3 were cultured at 37° C. for 20 hours in a carbon dioxide gas cell incubator, in 100 μl of RPMI-1640 medium (produced by Sigma) containing 50 IU/ml of penicillin (produced by Flow Laboratories, Scotland), 50 μg/ml of streptomycin (produced by Flow Laboratories), and 10% fetal bovine serum. After that, FE399-P1 or FE399-P2 was added thereto at an appropriate concentration, followed by further cultivation for 3 days. However, as for P388 and K562, the FE399 compound group was added immediately after preparation of cell culture liquids. Each of the cultures was added with 10 μl of a solution of MTT (3-(4,5-dimethyl-2-thiazolyl)-2,5-diphenyl-2H-tetrazolium.Br, 5 mg/ml Dulbecco PBS(-)), followed by cultivation at 37° C. for 4 hours in the carbon dioxide gas incubator. After that, each of the cultures was added with 50 μl of 0.01N hydrochloric acid/ 20% SDS, and then the absorbance was measured at 570 nm by using a microplate reader (reference wavelength: 630 nm). The concentration of the sample (IC$_{50}$), at which the cell proliferation is inhibited by 50%, is shown in Table 4.

TABLE 4

| Cell | Origin | Cell conc. (cells/ml) | IC$_{50}$ (ng/ml) FE399-P1 | FE399-P2 |
|---|---|---|---|---|
| SW948 | human colon cancer | 5 × 10$^4$ | 150 | 75 |
| K562T | human leukemia | 4 × 10$^4$ | 310 | 150 |

TABLE 4-continued

| Cell | Origin | Cell conc. (cells/ml) | IC$_{50}$ (ng/ml) FE399-P1 | FE399-P2 |
|---|---|---|---|---|
| Colon26 | mouse colon cancer | $5 \times 10^4$ | 400 | 150 |
| CHO-K1 | Chinese hamster ovary fibroblast | $1.5 \times 10^4$ | 300 | 120 |
| P388 | mouse leukemia | $2 \times 10^4$ | 360 | 130 |

As shown in Table 4, it is clear that the FE399 compounds of the present invention have the proliferation-inhibiting action on the cancer cells and the tumor cells of the various types.

Example 4: Anticancer Effect of FE399 Compound Group on Solid Cancer

Mouse colon cancer cells (colon-26) subcultured in vivo subcutaneously in a CDFI mouse were excised from the subcutaneous portion of the mouse. The cells were minced and transplanted subcutaneously with a trocar to CDFI mice (female, 4 weeks old) so that the concentration was 10 mg/mouse. The day of the transplantation was designated as 0th day. On 7th day, the tumor size and the body weight were measured, and the mice were classified into groups with n=4. The tumor size was calculated as a tumor weight in accordance with the following arithmetic expression.

Tumor weight (mg) = Tumor volume (mm$^3$) =

1/2 × long diameter (mm) × short diameter (mm)$^2$

FE399 which was obtained by drying up the acetonitrile solution of FE399-1 isolated by the method described in Example 1 under a reduced precondition was administered to the mice described above in accordance with the following schedule. FE399 was administered intraperitoneally in an administration amount of 0.2 mL/mouse. FE399 was dissolved in dimethyl sulfoxide (DMSO) so that the concentration was 100 mg/ml. The concentration was adjusted with physiological saline containing 5% Tween 80 so that the administration amount was 4 mg/kg or 8 mg/kg.

Administration was performed on every day of 7th day to 11th day and 14th day to 18th day (total 10 times) in the case of evaluation for the amount of 4 mg/kg. In the case of evaluation for the amount of 8 mg/kg, administration was performed on 7th day, 11th day, 14th day, and 18th day (total 4 times).

Mice, to which no FE399 was administered, were used as a control group. As comparative control, cisplatin was administered on 7th day, 11th day, and 15th day in an amount of 5 mg/kg. FE399 used for the experiment was a mixture of FE399-P1 and FE399-P2.

The anticancer effect was evaluated on the basis of the tumor enhancement inhibitory ratio (IR) calculated from the tumor weight. IR was determined in accordance with the following arithmetic expression.

$$IR(\%) = \left(1 - \frac{\text{tumor weight of administered group}}{\text{tumor weight control group}}\right) \times 100$$

Table 5 shows IR's (15th day and 21st day) for the respective administration doses. According to the result shown in Table 5, it has been demonstrated that the FE399 compound also exhibits the anticancer action in vivo.

TABLE 5

| Administration dose, administration times | IR (15th day) | IR (21st day) |
|---|---|---|
| 4 mg/kg × 10 | 47 | 38 |
| 8 mg/kg × 4 | 61 | 47 |
| cisplatin (5 mg/kg) | 63 | 73 |

Industrial Applicability

According to the present invention, the novel compounds having the antitumor activity are provided.

What is claimed is:

1. A compound represented by the following structural formula:

2. The compound according to claim 1, which is separated under the following development condition on thin layer chromatography:
   adsorbent: Kieselgel 60 F254, thickness: 0.25 mm;
   solvent for development: chloroform:methanol=93:7;
   Rf value: about 0.32.

3. The compound according to claim 1, which is separated under the following development condition on thin layer chromatography:
   adsorbent: Kieselgel 60 F254, thickness: 0.25 mm;
   solvent for development: chloroform:methanol=93:7;
   Rf value: about 0.42.

4. The compound according to claim 1, which is separated under the following development condition on thin layer chromatography:
   adsorbent: Kieselgel 60 F254, thickness: 0.25 mm;
   solvent for development: chloroform:methanol=93:7;
   Rf value: about 0.54.

5. A tautomeric equilibrium mixture comprising two or three tautomers of the compound defined in claim 1.

6. A tautomeric equilibrium mixture of claim 5, wherein the tautomers are selected from the group consisting of
   (a) a compound which is separated under the following development condition on thin layer chromatography:
      adsorbent: Kieselgel 60 F254, thickness: 0.25 mm;
      solvent for development: chloroform:methanol=93:7;
      Rf value: about 0.32,
   (b) a compound which is separated under the following development condition on thin layer chromatography:
      adsorbent: Kieselgel 60 F254, thickness: 0.25 mm;
      solvent for development: chloroform:methanol=93:7;
      Rf value: about 0.42, and
   (c) a compound which is separated under the following development condition on thin layer chromatography:
      adsorbent: Kieselgel 60 F254, thickness: 0.25 mm;
      solvent for development: chloroform:methanol=93:7;
      Rf value: about 0.54.

7. A method for producing a compound or a tautomeric mixture of compounds, comprising the steps of cultivating a mold belonging to the genus Ascochyta with a medium, and collecting, from an obtained culture, the compound defined in claim 1 or a tautomeric equilibrium mixture comprising two or three tautomers of the compound defined in claim 1.

8. The method of claim 7, wherein the tautomers are selected from the group consisting of
   (a) a compound which is separated under the following development condition on thin layer chromatography: adsorbent: Kieselgel 60 F254, thickness: 0.25 mm; solvent for development: chloroform:methanol=93:7; Rf value: about 0.32,
   (b) a compound which is separated under the following development condition on thin layer chromatography: adsorbent: Kieselgel 60 F254, thickness: 0.25 mm; solvent for development: chloroform:methanol=93:7; Rf value: about 0.42, and
   (c) a compound which is separated under the following development condition on thin layer chromatography: adsorbent: Kieselgel 60 F254, thickness: 0.25 mm; solvent for development: chloroform:methanol=93:7; Rf value: about 0.54.

9. A pharmaceutical composition comprising as an effective component the compound defined in claim 1, or a mixture of two or more tautomers of the compound defined in claim 1.

10. The pharmaceutical composition of claim 9, wherein the tautomer or tautomers is/are selected from the group consisting of
   (a) a compound which is separated under the following development condition on thin layer chromatography: adsorbent: Kieselgel 60 F254, thickness: 0.25 mm; solvent for development: chloroform:methanol=93:7; Rf value: about 0.32,
   (b) a compound which is separated under the following development condition on thin layer chromatography: adsorbent: Kieselgel 60 F254, thickness: 0.25 mm; solvent for development: chloroform:methanol= 93:7; Rf value: about 0.42, and
   (c) a compound which is separated under the following development condition on thin layer chromatography: adsorbent: Kieselgel 60 F254, thickness: 0.25 mm; solvent for development: chloroform:methanol=93:7; Rf value: about 0.54.

* * * * *